United States Patent [19]

Umezawa et al.

[11] Patent Number: 4,518,802

[45] Date of Patent: May 21, 1985

[54] N-[4-[(3-AMINOPROPYL)AMINO]BUTYL]-2,2-DIHYDROXYETHANAMIDE

[75] Inventors: Hamao Umezawa; Tomio Takeuchi, both of Tokyo; Shinichi Kondo, Yokohama; Hironobu Iinuma; Daishiro Ikeda, both of Tokyo; Teruya Nakamura, Kusatsu; Akio Fujii, Kamakura, all of Japan

[73] Assignee: Zaidan Hojin Biseibutsu Kagaku Kenkyu Kai, Tokyo, Japan

[21] Appl. No.: 583,563

[22] Filed: Feb. 27, 1984

Related U.S. Application Data

[63] Continuation of Ser. No. 375,916, May 7, 1982, abandoned.

[30] Foreign Application Priority Data

May 18, 1981 [JP] Japan .................................. 56-73510

[51] Int. Cl.³ .......................................... C07C 103/16
[52] U.S. Cl. ................................................. 564/201
[58] Field of Search ......................... 564/201; 424/309

[56] References Cited

U.S. PATENT DOCUMENTS

| | | | |
|---|---|---|---|
| 3,436,463 | 4/1969 | Mayhew et al. | 424/320 |
| 4,041,077 | 8/1977 | Ghosez et al. | 260/562 |
| 4,334,097 | 6/1982 | Schmidt | 564/201 |
| 4,416,899 | 11/1983 | Umezawa et al. | 424/320 |
| 4,430,346 | 2/1984 | Umezawa et al. | 424/311 |

OTHER PUBLICATIONS

*J. Antibiotics:* 29(4), 390–393, (1976)—Shoji et al.
*J. Antibiotics:* 34(12), 1622–1624, (1981)—Umezawa et al.
*J. Antibiotics:* 34(12), 1625–1627, (1981)—Kondo et al.

*Primary Examiner*—Robert V. Hines
*Attorney, Agent, or Firm*—Robert E. Carnahan

[57] ABSTRACT

N-[4-[(3-aminopropyl)amino]butyl]-2,2-dihydroxyethanamide is an immunostimulant in animals and an intermediate for synthesis of the antibiotic BMG162-aF2.

2 Claims, No Drawings

N-[4-[(3-AMINOPROPYL)AMINO]BUTYL]-2,2-DIHYDROXYETHANAMIDE

REFERENCE TO RELATED APPLICATION

This application is a continuation of copending application Ser. No. 375,916 filed May 7, 1982, and now abandoned.

SUMMARY OF THE INVENTION

This invention relates to N-[4-[(3-aminopropyl)amino]butyl]-2,2-dihydroxyethanamide of the formula (I)

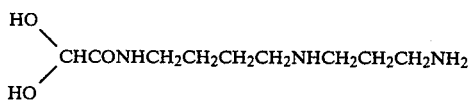       I and acid addition salts thereof and to a process for their synthesis.

BACKGROUND OF THE INVENTION

Umezawa et al. in application Ser. No. 297,458 now U.S. Pat. No. 4,416,899 filed Aug. 28, 1981 described the new antibiotic BMG162-aF2, its production by fermentation and isolation thereof from fermentation broths. The present inventors in application Ser. No. 375,950 now U.S. Pat. No. 4,430,346 (Japanese Application No. 69340/81 filed May 11, 1981) filed herewith describe a method for the synthesis of a new stereoisomer of BMG162-aF2 referred to therein as GHA-GS, and the antitumor properties of GHA-GS. The present invention provides an intermediate needed for that synthesis.

DETAILED DESCRIPTION OF THE INVENTION

This novel compound of this invention is useful as an intermediate for the synthesis of the antibiotic BMG162-aF2, and its new stereoisomer GHA-GS, N-[4-[(3-aminopropyl)amino]butyl]-2-[(S)-7-guanidino-3-hydroxy-heptanamido]-2-hydroxyethanamide, or a derivative thereof, and possesses immunostimulant properties in animals.

In view of its lack of stability, the novel compound of the present invention is prepared preferably in the form of an acid addition salt. The acids to be added include inorganic acids such as hydrochloric acid, sulfuric acid, phosphoric acid and boric acid, and organic acids such as acetic acid, citric acid, tartaric acid and glutaric acid. Of these acids, particularly preferred are hydrochloric acid, sulfuric acid and acetic acid.

The physiochemical and biological properties of the present compound are as shown below.

(1) Physicochemical properties.

The hydrochloride of the present compound is a white powder which shows no distinct melting point. The elementary analysis coincides with the theoretical calculated for $C_9H_{21}N_3O_3 \cdot 2HCl$ (C 36.99%, H 7.93%, N 14.38%, Cl 24.27%). The proton magnetic resonance (NMR), as measured in heavy water, shows characteristic signals at $\delta = 2.1$ (2-, 3-$CH_2$), 2.4–2.7 (2'-$CH_2$), 3.5–3.8 (1-, 4-, 1', 3'-$CH_2$), 5.77 (2''-CH, s).

(2) Biological properties.

The effect of the present compound (hydrochloride) on delayed hypersensitivity to sheep red blood corpuscle is as shown in Table 1. The test was performed according to the method of Mackaness et al. [Lagrange, P. H., Mackaness, G. B. and Miller, T. E., J. Exp. Med., 139, 528–542 (1974)] in the following manner.

Female $CDF_1$ mice, 6 weeks of age, were immunized by the intravenous injection of each with $10^5$ sheep red blood corpuscles and, at the same time, administered with varied amounts of the compound of formula (I) (hydrochloride) by intraperitoneal injection. After 4 days, each mouse was administered with $10^8$ sheep red blood corpuscles by subcutaneous injection to induce the reaction. After 24 hours, the swelling of footpad of each mouse was measured by means of slide calipers.

TABLE 1

Effect on Delayed Hypersensitivity

| Immunization | Compound of formula (I) (μg/mouse, i.p.) | Increase of footpad thickness (× 0.1 mm ± S.D.) | T/C (%) |
|---|---|---|---|
| $10^5$ SRBC* | none | 8.0 ± 0.7 | 100 |
| $10^5$ SRBC | 1 | 13.0 ± 1.7 | 163 |
| " | 4 | 13.0 ± 0.5 | 163 |
| " | 16 | 13.4 ± 0.6 | 168 |
| " | 63 | 14.9 ± 0.9 | 186 |
| " | 250 | 11.8 ± 0.6 | 148 |
| " | 1000 | 11.7 ± 1.0 | 146 |

*sheep red blood cells

As seen from Table 1, the reaction was enhanced by the administration of 1 μg to 1 mg of the compound of formula (I).

The present compound N-[4-[(3-aminopropyl)aminobutyl]-2,2-dihydroxyethanamide of the formula (I)

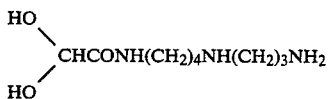       I is synthesized in the following manner.

A compound represented by the formula (II)

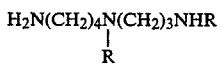       II (wherein R represents an amino-protective group such as benzyloxycarbonyl, chloroacetyl or a lower alkyloxycarbonyl) is allowed to condense with a dialkylacetal of glyoxylic acid represented by the formula (III)

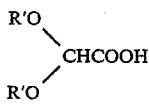       III (wherein R' represents an alkyl group of 1 to 5 carbon atoms) or a *reactive derivative of the carboxyl group of said dialkylacetal,* and thereafter the amino-protective group and the group R' are removed to yield the compound of formula (I).

The condensation of the compound of formula (II) with the compound of formula (III) or its reactive derivative is effected by the method for forming an ordinary amide linkage in the peptide synthesis by utilizing, for example, an acyl halide, acid azide, active ester, or acid anhydride. Thus, the condensation is conducted in the presence of a peptide synthesis carboxyl activating agent for the carboxyl group of the compound of formula (III). Examples of the suitable carboxyl activating reagents used for the activation of carboxyl group or the formation of a reactive derivative include reagents for forming active esters such as 6-chloro-1-p-chlorobenzenesulfonyloxybenzotriazole (CCBT), N-ethyl-5-phenylisoxazolium-3′-sulfonate (NEPIS), N-tert-butyl-5-methylisoxazolium perchlorate, N-ethoxycarbonyl-2-ethoxy-1,2-dihydroquinoline, di-p-nitrophenyl sulfite, tri-p-nitrophenyl phosphite, p-nitrophenyl trichloroacetate, N-hydroxysuccinimide, p-nitrophenol, pentachlorophenol, and benzyl alcohol; carbodiimides such as dicyclohexylcarbodiimide (DDC), 1-ethyl-3-(3-dimethylaminopropyl)carbodiimide, 1-cyclohexyl-3-(2-morpholinoethyl)carbodiimide, di-p-toluylcarbodiimide, and diisopropylcarbodiimide; and reagents for azide synthesis.

The condensation reaction is carried out preferably in an organic solvent such as ethyl acetate and at a temperature of generally 0° to 100° C., preferably 10° to 40° C. Although the reaction time varies with the reaction temperature, it is about 5 to about 30 hours at room temperature. The amount used of the carboxylic acid of formula (III) or a reactive derivative thereof is 0.5 to 10 moles, preferably 2 to 5 moles per mole of the amine of formula (II).

The removal of protective groups from the condensate formed as described above can be performed by hydrolysis or reduction according to the type of protective group, but those protective groups which are removable by acid hydrolysis are preferable. For instance, when the amino-protective group is tert-butoxycarbonyl group and the aldehyde-protective group is diethylacetal, the hydrolysis is conducted in an aqueous dioxane solution by adding 2 to 3 equivalents of dilute hydrochloric acid and heating at 100° C. for 2 to 5 hours to obtain hydrochloride of the present compound of formula (I). When the amino-protective group is benzyloxycarbonyl group, the removal of the protective group is effected preferably by hydrogenolysis using palladium platinum oxide, or the like.

The starting compound of the formula (II)

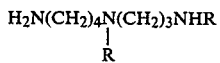  II (where R is an amino-protective group) is difficult to obtain in a good yield by introducing selectively two amino-protective groups into spermidine. Accordingly, it is prepared by condensing in a customary manner a monoamino-protected 1,4-butanediamine of the formula (IV)

R″HN(CH$_2$)$_4$NH$_2$   IV (where R″ is an amino-protective group different from the above-noted R) with an amino-protected 3-halopropanamine of the formula (V)

X(CH$_2$)$_3$NHR   V (where R is the same amino-protective group as noted above and X is a halogen atom) to form a compound of the formula (VI)

R″HN(CH$_2$)$_4$NH(CH$_2$)$_3$NHR   VI (where R and R″ are amino-protective groups different from each other), then protecting the remaining imino group with the same amino-protective group as R, and selectively removing another amino-protective group R″ to obtain the compound of formula (II).

Alternatively, the compound of the formula (VI) is obtained by condensing monoamino-protected 1,3-propanediamine of the formula (VII)

RHN(CH$_2$)$_3$NH$_2$   VII (wherein R is as defined above) with an amino-protective 4-halobutanamine of the formula (VIII)

X(CH$_2$)$_4$NHR″   VIII (wherein R″ and X are as defined above) in a manner as described above.

For the protection of amino groups, those amino-protective groups which are customarily used in the peptide synthesis can be utilized, but the amino-protective group of R″ should be selectively removable, leaving behind the amino-protective group of R. Accordingly, a combination of a benzyloxycarbonyl group removable by hydrogenolysis and a tert-butoxycarbonyl group removable by the weak acid treatment is a most preferable example. Either one of this pair may be R or R″.

The condensation of a compound of formula (IV) with a compound of formula (V) or the condensation of a compound of formula (VII) with a compound of formula (VIII) is easily conducted in an anhydrous solvent such as N,N-dimethylformamide at room temperature in the presence of triethylamine. The halogen in the compound of formula (VIII) is preferably bromine.

The dialkylacetal of glyoxylic acid of formula (III) is easily formed by reacting glyoxylic acid with an alkanol using an acid catalyst in a customary manner. Suitable alkanols for use are methanol, ethanol, propanol, butanol and amyl alcohol. The dialkylacetal of formula (III) is also conveniently obtained by the alkaline hydrolysis of commercial ethyl 2,2-diethoxyacetate.

Starting from the present compound of formula (I), N-[4-[(3-aminopropyl)amino]butyl]-2-[(S)-7-guanidino-3-hydroxyheptanamido]-2-hydroxyethanamide (referred to as GHA-GS in our co-pending application Ser. No. 375,950) is synthesized by the condensation of the present compound of the formula (I) with (S)-7-guanidino-3-hydroxyheptanamide of the formula

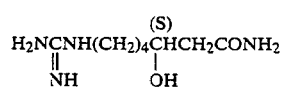

by heating the compounds together in the presence of an inorganic or organic acid.

The invention is illustrated below with reference to example but the invention is not limited thereto.

EXAMPLE (a) Synthesis of mono-N-benzyloxycarbonyl-1,4-butanediamine.

Into 30 mL of 50% aqueous methanol, was dissolved 1.76 g (20 mmoles) of 1,4-butanediamine followed by the addition of 5.48 g (20 mmoles) of S-benzyloxycarbonyl-4,6-dimethyl-2-mercaptopyrimidine (a product of Kokusan Kagaku Co.). The mixture was stirred for 3 hours. Thereafter, the reaction mixture was filtered to remove the precipitated di-N-benzyloxycarbonyl compound [2.09 g (29%) were recovered], and the filtrate was evaporated to dryness. The residue was dissolved in 250 mL of chloroform, washed 5 times with 100 mL of water. The chloroform layer was dried over anhydrous sodium sulfate, and evaporated to dryness to obtain 1.0 g (23% yield) of mono-N-benzyloxycarbonyl-1,4-butanediamine in colorless syrup form.

(b) Synthesis of O-tosyl-3-tert-butoxycarbonylamino-1-propanol.

Into 30 mL of methanol, was dissolved 1.5 g (20 mmoles) of 3-amino-1-propanol followed by the addition of 4.8 g (20 mmoles) of tert-butyl S-4,6-dimethylpyrimid-2-yl thiocarbonate (a product of Kokusan Kagaku Co.). The mixture was stirred for 6 hours. The reaction mixture was evaporated to dryness, dissolved in 200 mL of chloroform, and washed with 200 mL of water. The chloroform layer was concentrated and subjected to column chromatography using 300 g of silica gel (Wako-Gel ®C-200) and a toluene-ethyl acetate (1:1 by volume) mixture as developing solvent. Fraction Nos. 82 to 151 (each 15 mL in volume) were combined, evaporated to dryness to obtain 2.95 g (84% yield) of 3-tert-butoxycarbonylamino-1-propanol in colorless oily form.

Into 50 mL of pyridine was dissolved 2.95 g (16.9 mmoles) of 3-tert-butoxycarbonylamino-1-propanol. To the solution, while being cooled in ice under an argon atmosphere, was added dropwise over a period of 40 minutes a solution of 3.36 g (17.7 mmoles) of p-toluenesulfonyl chloride in pyridine. The mixture was left standing overnight at 7° C., then admixed with a small volume of water, and evaporated to dryness. The residue was dissolved in 200 mL of chloroform, washed successively with 5% aqueous potassium hydrogensulfate solution, saturated aqueous sodium hydrogencarbonate solution, and water, then dried over anhydrous sodium sulfate, evaporated to dryness, and subjected to column chromatography using 120 g of silica gel (Wako-Gel ®C-200) and a toluene-ethyl acetate (8:1 by volume) mixture as developing solvent. Fraction Nos. 35 to 68 (each 15 mL in volume) were combined and evaporated to dryness to yield 3.06 g (55% yield) of O-tosyl-3-tert-butoxycarbonylamino-1-propanol in colorless oily form.

(c) Synthesis of N-tert-butoxycarbonyl-N'-(tert-butoxycarbonylaminopropyl)-1,4-butanediamine.

Into 15 mL of dimethylformamide was dissolved 800 mg (2.43 mmoles) of O-tosyl-3-tert-butoxycarbonylamino-1-propanol obtained in (b) above. After addition of 510 mg (4.8 mmoles) of lithium bromide (LiBr.H2O), the solution was stirred at room temperature for 24 hours. To the reaction mixture containing the bromo derivative were added 540 mg (2.43 mmoles) of mono-N-benzyloxycarbonyl-1,4-butanediamine obtained in (a) above and 0.34 mL of triethylamine. The mixture was stirred at room temperature for 48 hours. The reaction mixture was admixed with 699 mg (2.9 mmoles) of tert-butyl S-4,6-dimethylpyrimid-2-yl thiocarbonate and stirred at room temperature for 13 hours. The reaction mixture was evaporated to dryness, dissolved in 100 mL of chloroform, washed with 50 mL of water, dried over anhydrous sodium sulfate, and evaporated to dryness. The residue was subjected to column chromatography using 200 g of silica gel (Wako-Gel ®C-200) and a toluene-ethyl acetate (4:1 by volume) mixture as developing solvent. Fraction Nos. 134 to 165 (each 12 mL in volume) were combined and evaporated to dryness to obtain 608 mg (52% yield) of N-benzyloxycarbonyl-N'-tert-butoxycarbonyl-N'-(tert-butoxycarbonylaminopropyl)-1,4-butanediamine in colorless syrup form.

Into 5 mL of methanol was dissolved 144 mg (0.3 mmole) of the above compound in colorless syrup form. After addition of 100 mg of 5% palladium-barium carbonate, the mixture was stirred at room temperature for 5 hours under a hydrogen stream, freed from the catalyst by filtration, and evaporated to dryness to yield 103 mg (100% yield) of N-tert-butoxycarbonyl-N'-(tert-butoxycarbonylaminopropyl)-1,4-butanediamine.

(d) Synthesis of N-[4-[(3-aminopropyl)amino]butyl]-2,2-dihydroxyethanamide.

Into 2 mL of ethyl acetate were dissolved 100 mg (0.29 mmole) of N-tert-butoxycarbonyl-N'-(tert-butoxycarbonylaminopropyl)-1,4-butanediamine obtained in (c) above and 148 mg (1 mmole) of 2,2-diethoxyacetic acid. After addition of 135 mg (1 mmole) of 1-hydroxybenzotriazole and 206 mg (1 mmole) of dicyclohexylcarbodiimide, the mixture was stirred at room temperature for 15 hours. The reaction mixture was filtered to remove the precipitate and the precipitate was washed with cold ethyl acetate. The filtrate and the washings were combined and washed successively with 1M aqueous ammonia and water. The ethyl acetate layer was dried over anhydrous sodium sulfate, and evaporated to dryness. The residue was subjected to column chromatography using 20 g of silica gel (Wako-Gel ®C-200) and a toluene-ethyl acetate (1:2 by volume) mixture as developing solvent. The Fraction Nos. 14 to 21 (each 3 mL in volume) were combined and evaporated to dryness to yield 109 mg (79% yield) of N-[N-(3-tert-butoxycarbonylaminopropyl)-4-(tert-butoxycarbonylamino)-butyl]-2,2-diethoxyethanamide as a colorless syrupy substance.

Into 1 mL of dioxane was dissolved 44 mg (0.13 mmole) of the above syrupy substance. After addition of 2.5 mL of 0.1N hydrochloric acid, the mixture was stirred for 4 hours in an oil bath heated at 100° C. The reaction mixture was adjusted to pH 6 with 0.2N aqueous sodium hydroxide solution and evaporated to dryness. The residue was extracted with 1.5 mL of methanol. The extract was passed through a column (16.5 mm in inner diameter) packed with 100 mL of Sephadex ®LH-20 and developed with methanol. Fraction Nos. 22 to 25 (each 2 mL in volume) positive to ninhydrin test were combined and evaporated to dryness to obtain 13 mg (46% yield) of N-[4-[(3-aminopropyl)amino)butyl]-2,2-dihydroxyethanamide dihydrochloride in colorless syrup form.

The method for the condensation of this material with (S)-7-guanidino-3-hydroxyheptanamide and the method for preparation of the latter are disclosed in Example 1 and Procedure 1 respectively of our copending application. Example 1 and Procedure 1 of Ser. No. 375,950 are incorporated herein by reference.

We claim:

1. A compound selected from the group consisting of N-[4-[(3-aminopropyl)amino]butyl]-2,2-dihydroxyethanamide of the formula (I)

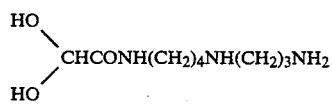

and an acid addition salt thereof.

2. A compound according to claim 1, wherein the acid addition salt is the hydrochloride.

* * * * *